(12) United States Patent
Badie et al.

(10) Patent No.: US 11,207,525 B2
(45) Date of Patent: *Dec. 28, 2021

(54) METHOD AND DEVICE FOR DISCRIMINATION OF LEFT VENTRICULAR PSEUDO-FUSION PACING

(71) Applicant: Pacesetter, Inc., Sylmar, CA (US)

(72) Inventors: Nima Badie, Berkeley, CA (US); Jan Mangual-Soto, Rho (IT); Luke McSpadden, Los Angeles, CA (US); Aditya Goil, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 111 days.

This patent is subject to a terminal disclaimer.

(21) Appl. No.: 16/740,547

(22) Filed: Jan. 13, 2020

(65) Prior Publication Data

US 2020/0147395 A1    May 14, 2020

Related U.S. Application Data

(63) Continuation of application No. 15/851,372, filed on Dec. 21, 2017, now Pat. No. 10,569,091.

(51) Int. Cl.
*A61N 1/36* (2006.01)
*A61N 1/365* (2006.01)
(Continued)

(52) U.S. Cl.
CPC ......... *A61N 1/36514* (2013.01); *A61N 1/025* (2013.01); *A61N 1/0563* (2013.01);
(Continued)

(58) Field of Classification Search
USPC ........................................... 607/17
See application file for complete search history.

(56) References Cited

U.S. PATENT DOCUMENTS

| 6,832,112 B1 | 12/2004 | Bornzin |
| 6,928,326 B1 | 8/2005 | Levine |

(Continued)

OTHER PUBLICATIONS

Ghosh et al. "Automated Detection of Effective Left-Ventricular Pacing: Going Beyond Percentage Pacing Counters" Europace (2015) 17; 8 pages.

(Continued)

*Primary Examiner* — Nicole F Lavert
*Assistant Examiner* — Nicole F Johnson
(74) *Attorney, Agent, or Firm* — The Small Patent Law Group LLC; Dean D. Small

(57) ABSTRACT

Methods and devices are provided for, under control of one or more processors within an implantable medical device (IMD), delivering cardiac resynchronization therapy (CRT) at one or more pacing sites. The processors obtain cardiac signals, associated with a candidate beat, from multi-site left ventricular (MSLV) electrodes distributed along a left ventricle and analyze the cardiac signals to collect at least one of a MSLV conduction pattern or a MSLV morphology. The processors compare at least one of the MSLV conduction pattern or MSLV morphology to one or more associated templates. The processors then label the candidate beat as a pseudo-fusion beat based on the comparing and adjust the CRT based on the labeling.

24 Claims, 9 Drawing Sheets

(51) Int. Cl.
  *A61N 1/362*  (2006.01)
  *A61N 1/37*   (2006.01)
  *A61N 1/368*  (2006.01)
  *A61N 1/02*   (2006.01)
  *A61N 1/05*   (2006.01)

(52) U.S. Cl.
  CPC ....... *A61N 1/3627* (2013.01); *A61N 1/36507* (2013.01); *A61N 1/36842* (2017.08); *A61N 1/36843* (2017.08); *A61N 1/371* (2013.01)

(56) References Cited

U.S. PATENT DOCUMENTS

| | | | |
|---|---|---|---|
| 7,509,170 B2 | 3/2009 | Zhang et al. | |
| 8,391,980 B2 | 3/2013 | Bornzin et al. | |
| 8,831,747 B1 | 9/2014 | Min et al. | |
| 9,044,610 B2 | 6/2015 | Rosenberg et al. | |
| 9,216,285 B1 | 12/2015 | Boling et al. | |
| 9,232,485 B2 | 1/2016 | Schwartz et al. | |
| 9,333,351 B2 | 5/2016 | Arnold et al. | |
| 2005/0043895 A1* | 2/2005 | Schechter | A61B 8/0883 702/19 |
| 2005/0013147 A1 | 6/2005 | Kim et al. | |
| 2005/0131476 A1 | 6/2005 | Kim et al. | |
| 2009/0005832 A1* | 1/2009 | Zhu | A61N 1/3627 607/27 |
| 2009/0163973 A1 | 6/2009 | Meyer et al. | |
| 2010/3005646 | 12/2010 | Schulte et al. | |
| 2013/0296962 A1 | 11/2013 | Keel et al. | |
| 2014/0207013 A1 | 7/2014 | Lian et al. | |

OTHER PUBLICATIONS

Examination Report for related European Patent Application No. 18214078.0 dated Jul. 7, 2021 (5 pages).

* cited by examiner

METHOD AND DEVICE FOR DISCRIMINATION OF LEFT VENTRICULAR PSEUDO-FUSION PACING

REFERENCE TO RELATED APPLICATIONS

The present application is a continuation application of, and claims priority to, U.S. application Ser. No. 15/851,372, Titled "METHOD AND DEVICE FOR DISCRIMINATION OF LEFT VENTRICULAR PSEUDO-FUSION PACING" which was filed on Dec. 21, 2017 (now U.S. Pat. No. 10,569,091 issued Feb. 25, 2020), the complete subject matter of which is expressly incorporated herein by reference in its entirety.

BACKGROUND

Embodiments of the present disclosure generally relate to methods and devices for monitoring left ventricular (LV) pacing, and more particularly for discriminating pseudo-fusion LV pacing based on multiple LV electrode activation patterns and morphologies.

Cardiac resynchronization therapy (CRT) seeks to normalize asynchronous cardiac electrical activation and resultant asynchronous contractions associated with congestive heart failure (CHF) by delivering synchronized pacing stimulus to both ventricles of the heart. The stimulus is synchronized to improve overall cardiac function, and reduce the susceptibility to life-threatening tachyarrhythmias. CRT may involve pacing from the right ventricular (RV) apex, the transvenous LV (e.g., in the lateral or postero-lateral vein), and the right atrium (RA). Studies have suggested that biventricular (BiV) pacing from two LV sites results in a further improved clinical outcome in CRT patients, in comparison with conventional BiV pacing.

Multi-site LV (MSLV) pacing systems have been proposed that offer the flexibility of varying an interventricular RV-to-LV pacing delay (RVLV) as well as an intraventricular LV-to-LV pacing delay (LVLV). However, issues can arise when setting these or similar pacing delays. In particular, circumstances can arise where the delays are set too long such that propagation of electrical depolarization wave fronts from other pacing sites can interfere with MSLV pacing. In particular, the depolarization wave fronts can prevent capture of MSLV paced events delivered at sites in the LV or can fuse with events paced at those sites. In either case, inappropriate or ineffective CRT pacing can result. Also, circumstances can arise where the pacing might be proarrhythmic.

Effective CRT therapy involves a high percentage of ventricular pacing, particularly in the left ventricle (LV). However, ineffective LV pacing may result due to loss of LV capture and/or a presence of pseudo-fusion between the ventricular paced event and an intrinsic depolarization wave front. Loss of LV capture may be avoided with the use of periodic, device-based threshold tests to ensure adequate pacing amplitudes. However, pseudo-fusion represents a temporal phenomenon that can exist regardless of pacing amplitude. An LV paced event of sufficient amplitude may coincide with a depolarization wave front. The depolarization wave front may result from normal AV conduction. For example, a depolarization wave front from a normal AV conduction may experience pseudo-fusion with a ventricular paced event when the device has a programmed AV delay that is too long. As another example, a ventricular paced event may experience pseudo-fusion with a depolarization wave front that arises from an abnormal AV conduction (e.g., atrial fibrillation). As another example, an LV ventricular paced event may experience pseudo-fusion with a depolarization wave front that is initiated by an RV paced event, such as when the IMD has a programmed RV-LV delay that is too long. When an LV ventricular paced event experiences pseudo-fusion with a depolarization wave front, the LV ventricular paced event becomes very inefficient and does not achieve a desired response from the heart. Consequently, additional ventricular paced events may be delivered which result in unnecessary battery depletion. In some instances, pseudo-fusion may lead to a determination that the patient is nonresponsive to CRT.

Heretofore, surface ECG signals were used to determine whether LV pacing was effective or experienced pseudo-fusion with depolarization wave fronts. Recently a device-based algorithm has been proposed to distinguish between effective LV capture and pseudo-fusion. The device-based algorithm analyzes EGM signals collected along a LV cathode-to-RV coil vector during a predetermined (e.g., 170 ms) sensing window following an LV paced event. The device-based algorithm searches the sensed cardiac signal for a positive deflection in the LV EGM immediately after the delivery of an LV paced event. When the positive deflection occurs within the sensing window, the device-based algorithm declares pseudo-fusion present. The device-based algorithm declares effective LV pacing to occur based on the following rules: 1) the sensed cardiac signal exhibits a minimum valley at least 23 ms before a maximum peak, and 2) a ratio of maximum to minimum amplitudes (relative to a baseline amplitude at the delivery of LV pacing) is between 0.125 and 8. In other words, if the first positive deflection exists in the sensing window and is not preceded by a negative deflection, then the beat is classified as a pseudo-fusion beat.

However, the above noted device-based algorithm experiences certain disadvantages. The algorithm is only able to identify pseudo-fusion based on the above-noted limited criteria. However, pseudo-fusion may occur without a positive LV EGM deflection at the time of LV pacing. Thus, additional and more robust criteria are needed to identify pseudo-fusion even without a positive LV EGM deflection at a particular point in time.

SUMMARY

In accordance with embodiments herein, a method is provided comprising, under control of one or more processors within an implantable medical device (IMD), the delivery of cardiac resynchronization therapy (CRT) at one or more pacing sites. The processors obtain cardiac signals, associated with a candidate beat, from multi-site left ventricular (MSLV) electrodes distributed along a left ventricle and analyze the cardiac signals to collect at least one of a MSLV conduction pattern or MSLV morphology. The processors compare the at least one of the MSLV conduction pattern or MSLV morphology to one or more associated templates. The processors then label the candidate beat as a pseudo-fusion beat based on the comparing and adjust the CRT based on the labeling.

Optionally, the method may include delivering LV pacing, where the one or more pacing sites includes one or more LV pacing sites. The labeling further may comprise labeling the candidate beat as a capture beat when the at least one of the MSLV conduction pattern or MSLV morphology match the associated template.

Optionally, the method may further comprise generating a set of the templates by cycling through CRT parameters for intrinsic conduction, right ventricular-only pacing, LV-only pacing and Bi-ventricular (BiV) pacing. The method may further comprise sensing baseline cardiac signals from the MSLV electrodes in connection with each of the CRT parameters and analyzing the baseline cardiac signals to generate the set of templates. Each template from the set of templates may be generated based on averages for characteristics of interest from the cardiac signals for multiple beats associated with corresponding stimulus. The set of templates may comprise a set of morphology templates that include characteristics of interest from cardiac signals for multiple beats, the characteristics of interest including amplitudes of positive deflection local maximums, negative deflection local minimums, and zero crossings, the characteristics of interest further including characteristic timings with respect to a reference time-point.

Optionally, the conduction pattern may comprise mean LV activation times associated with sensing vectors corresponding to the MSLV electrodes, and wherein the mean LV activation times are relative to a right ventricular (RV) activation time. The LV activation times may further be associated with an RV-to-LVD1 activation interval, an RV-to-LVM2 activation interval, an RV-to-LVM3 activation interval, and an RV-to-LVP4 activation interval.

Optionally, the MSLV morphology may comprise unipolar or far-field morphologies for cardiac signals collected along sensing vectors that comprise at least one of RV-Can/Coil, LVD1-Can/Coil, LVM2-Can/Coil, LVM3-Can/Coil, or LVP4-Can/Coil. The method may further comprise adjusting at least one parameter that defines the CRT when the candidate beat is labeled the pseudo-fusion beat.

In accordance with embodiments herein, a system is provided comprising a lead having a multi-site left ventricular (MSLV) electrode combination, memory to store program instructions, one or more processors configured to implement the program instructions to perform delivery of cardiac resynchronization therapy (CRT) at one or more pacing sites from the MSLV electrode combination. The system obtains cardiac signals, associated with a candidate beat, from the MSLV electrodes distributed along a left ventricle and analyzing the cardiac signals to collect at least one of a MSLV conduction pattern or a MSLV morphology. The system compares the at least one of the MSLV conduction pattern or MSLV morphology to one or more associated templates, labels the candidate beat as a pseudo-fusion beat based on the comparing; and adjusts the CRT based on the labeling.

Optionally the one or more processors may be further configured to deliver LV pacing, the one or more pacing sites includes one or more LV pacing sites. The one or more processors may be further configured to label the candidate beat as a capture beat when the at least one of the MSLV conduction pattern or MSLV morphology match the associated template. The one or more processors may further be configured to generate a set of the templates by cycling through CRT parameters for intrinsic conduction, right ventricular-only pacing, LV-only pacing, and Bi-ventricular (BiV) pacing. The one or more processors may further be configured to sense baseline cardiac signals from the MSLV electrodes in connection with each of the CRT parameters and analyze the baseline cardiac signals to generate the set of templates.

Optionally, each template from the set of templates may be generated based on averages for characteristics of interest from the cardiac signals for multiple beats associated with corresponding stimulus. The set of templates may comprise a set of morphology templates that include characteristics of interest from cardiac signals for multiple beats, the characteristics of interest including amplitudes of positive deflection local maximums, negative deflection local minimums, and zero crossings, the characteristics of interest further including characteristic timings with respect to a reference time-point. The conduction pattern may comprise mean LV activation times associated with sensing vectors corresponding to the MSLV electrodes, and wherein the mean LV activation times are relative to a right ventricular (RV) activation time.

Optionally, the LV activation times may be associated with an RV-to-LVD1 activation interval, an RV-to-LVM2 activation interval, an RV-to-LVM3 activation interval, and an RV-to-LVP4 activation interval. The MSLV morphology may comprise unipolar or far-field morphologies for cardiac signals collected along sensing vectors that comprise at least one of RV-Can/Coil, LVD1-Can/Coil, LVM2-Can/Coil, LVM3-Can/Coil, or LVP4-Can/Coil. The one or more processors may be configured to adjust at least one parameter that defines the CRT when the candidate beat is labeled the pseudo-fusion beat.

DETAILED DESCRIPTION

Figure 1:
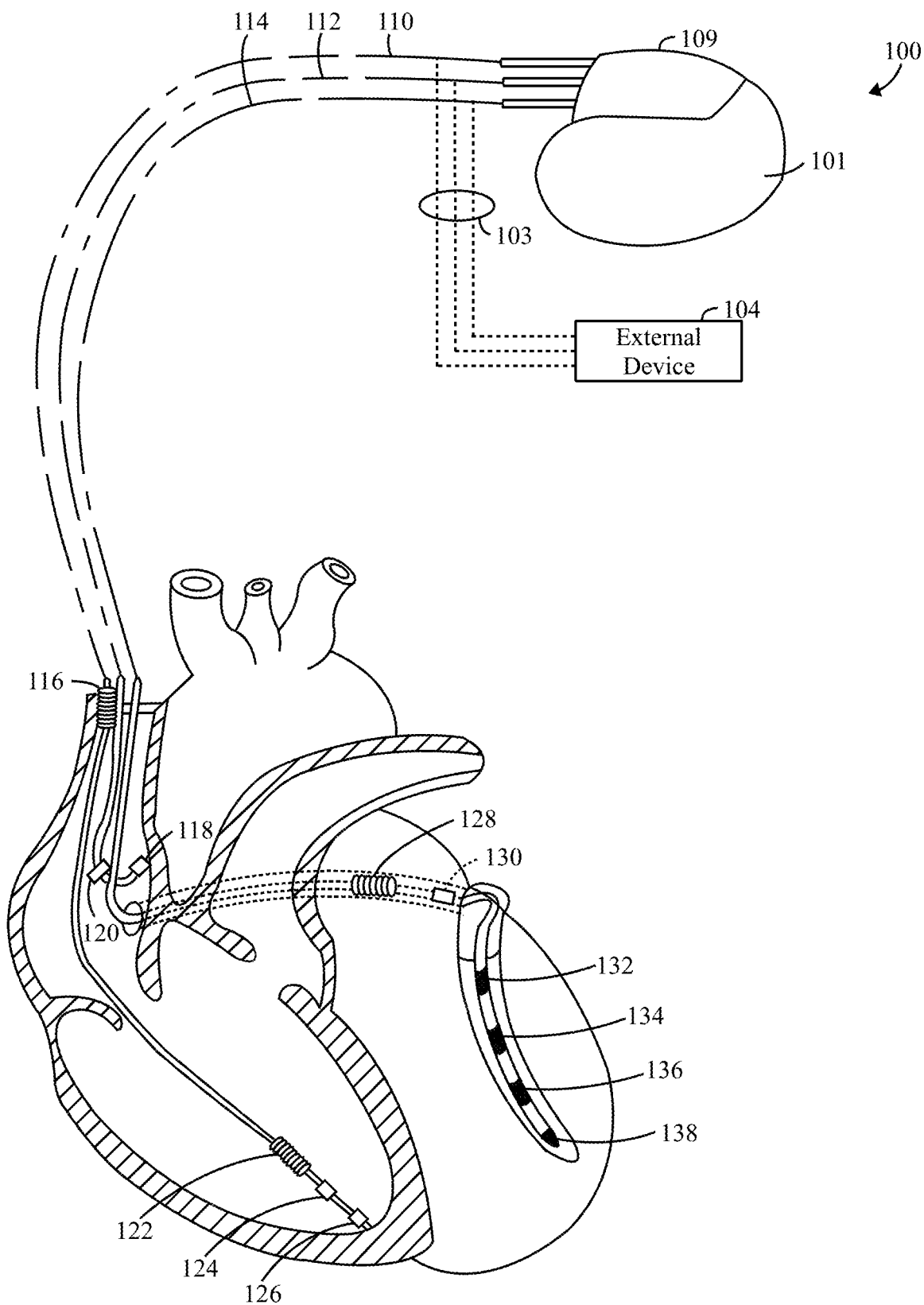
FIG. 1 illustrates an IMD and external device coupled to a heart in a patient and implemented in accordance with one embodiment.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

In accordance with an embodiment, methods and devices are provided that leverage the use of multiple LV electrodes (e.g., quadripolar CRT systems) to spatiotemporally characterize a propagating wave front in a comprehensive manner. Each propagating wave front arrives at the LV electrodes with a unique 3D wave front shape and incident angle. As a result, every unique stimulus origin (e.g., SA node, RV electrode, LVD1 electrode) can be described by a unique electrical signature comprised of an LV activation pattern and a collection of LV EGM morphologies. Embodiments herein utilize the electrical signatures to distinguish LV pseudo-fusion pacing from effective LV pacing based on (a) the conduction pattern across multiple LV electrodes and/or (b) the collection of EGM morphologies at multiple LV electrodes.

Methods and systems herein distinguish LV pseudo-fusion pacing from effective LV pacing by identifying the stimulus origin using the following electrical characteristics: (a) the conduction pattern across multiple LV electrodes and (b) the collection of EGM morphologies at multiple LV electrodes. The methods and systems leverage the existence of multisite LV (MSLV) electrodes to characterize the spatiotemporal dynamics of the propagating wave front, and do not simply rely on local voltage deflections at a single LV electrode.

The microcontroller responds by adjusting the various CRT parameters (such as rate, AV Delay, V-V Delay, etc.) at which the atrial and ventricle pacing pulses are administered.

FIG. 1 illustrates an IMD 100 and external device 104 coupled to a heart in a patient and implemented in accordance with one embodiment. The external device 104 may be a programmer, an external defibrillator, a workstation, a portable computer, a personal digital assistant, a cell phone, a bedside monitor and/or the like. The IMD may represent a cardiac monitoring device, pacemaker, cardioverter, cardiac rhythm management device, defibrillator, neurostimulator, leadless monitoring device, leadless pacemaker and/or the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 100 are discussed and illustrated in the drawings herewith.

The IMD 100 includes a housing 101 that is joined to a header assembly 109 that holds receptacle connectors connected to a right ventricular lead 110, a right atrial lead 112, and a coronary sinus lead 114, respectively. The leads 112, 114 and 110 measure cardiac signals of the heart. The right atrial lead 112 includes an atrial tip electrode 118 and an atrial ring electrode 120. The coronary sinus lead 114 includes a left atrial ring electrode 128, a left atrial coil electrode 130 and one or more left ventricular electrodes 132-138 (e.g., also referred to as LVD1, LVM2, LVM3 and LVP4) to form a multi-site LV (MSLV) electrode combination. The right ventricular lead 110 includes an RV tip electrode 126, an RV ring electrode 124, an RV coil electrode 122, and an SVC coil electrode 116. The leads 112, 114 and 110 detect IEGM signals that are processed and analyzed as described herein. The leads 112, 114 and 110 also delivery therapies as described herein.

During implantation, the external device 104 is connected to one or more of the leads 112, 114 and 110 through temporary inputs 103. The inputs 103 of the external device 104 receive IEGM signals from the leads 112, 114 and 110 during implantation and display the IEGM signals to the physician on a display. Optionally, the external device 104 may not be directly connected to the leads 112, 114 and 110. Instead, the IEGM cardiac signals sensed by the leads 112, 114 and 110 may be collected by the IMD 100 and then transmitted wirelessly to the external device 104. Hence, the external device 104 receives the IEGM cardiac signals through telemetry circuit inputs. The physician or another user controls operation of the external device 104 through a user interface.

Implantable Medical Device

Figure 2:
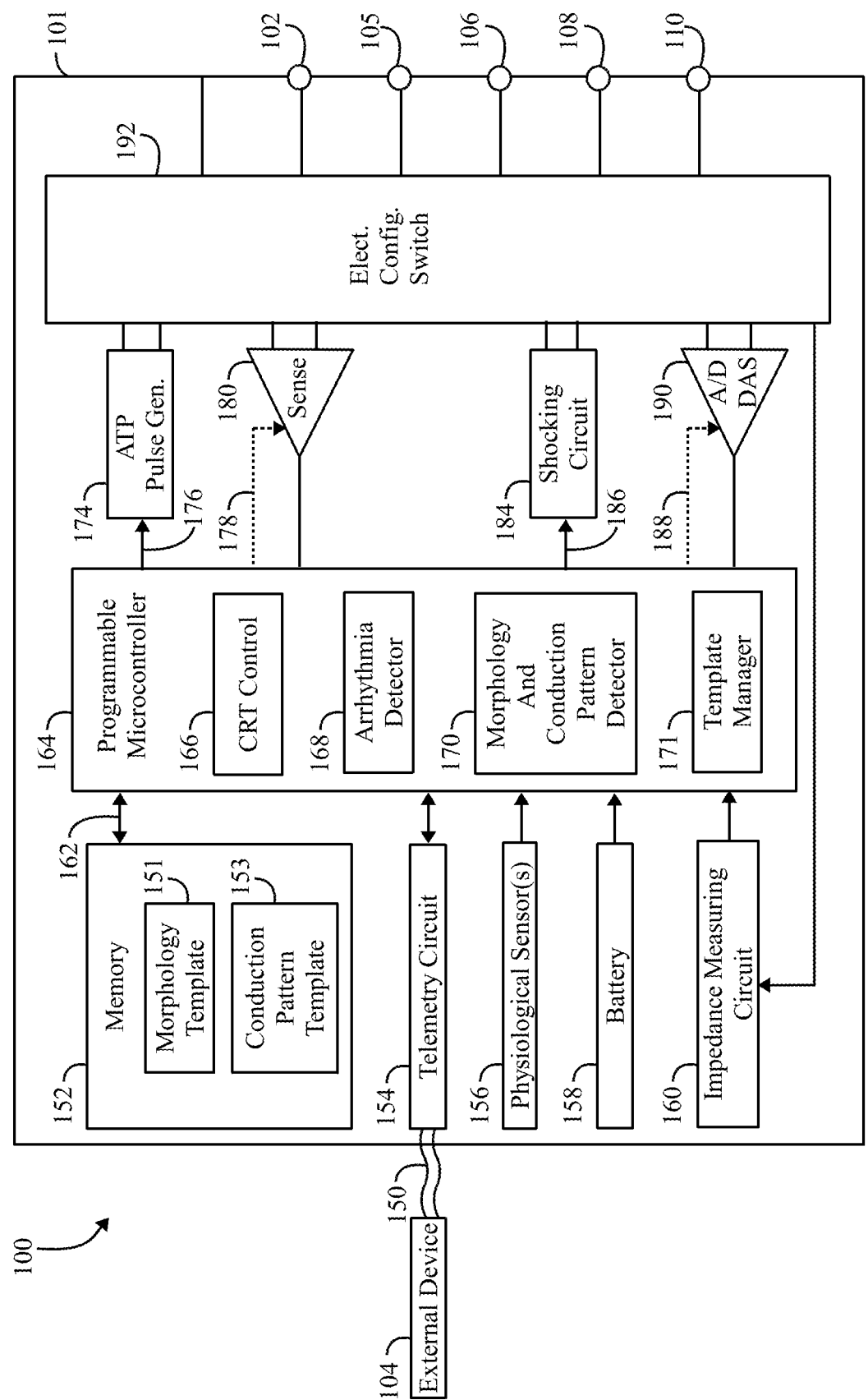
FIG. 2 shows an exemplary IMD that is implanted into the patient as part of the implantable cardiac system.

FIG. 2 shows an exemplary IMD 100 that is implanted into the patient as part of the implantable cardiac system. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing.

The IMD 100 has a housing 101 to hold the electronic/computing components. The housing 101 (which is often referred to as the "can", "case", "encasing", or "case electrode") may be programmably selected to act as the return electrode for certain stimulus modes. Housing 101 further includes a connector (not shown) with a plurality of terminals 102, 105, 106, 108, and 110. The terminals may be connected to electrodes that are located in various locations within and about the heart. For example, the terminals may include: a terminal 102 to be coupled to an first electrode (e.g., a tip electrode) located in a first chamber; a terminal 105 to be coupled to a second electrode (e.g., tip electrode) located in a second chamber; a terminal 106 to be coupled to an electrode (e.g., ring) located in the first chamber; a terminal 108 to be coupled to an electrode located (e.g., ring electrode) in the second chamber; and a terminal 110 to be coupled to an electrode (e.g., coil) located in the SVC. The type and location of each electrode may vary. For example, the electrodes may include various combinations of ring, tip, coil and shocking electrodes and the like.

The IMD 100 includes a programmable microcontroller 164 that controls various operations of the IMD 100, including cardiac monitoring and stimulation therapy. Microcontroller 164 includes a microprocessor (or equivalent control circuitry), RAM and/or ROM memory, logic and timing circuitry, state machine circuitry, and I/O circuitry.

IMD 100 further includes a first chamber pulse generator 174 that generates stimulation pulses for delivery by one or more electrodes coupled thereto. The pulse generator 174 is controlled by the microcontroller 164 via control signal 176. The pulse generator 174 is coupled to the select electrode(s) via an electrode configuration switch 192, which includes multiple switches for connecting the desired electrodes to the appropriate I/O circuits, thereby facilitating electrode programmability. The switch 192 is controlled by a control signal 186 from the microcontroller 164.

In the example of FIG. 2, a single pulse generator 174 is illustrated. Optionally, the IMD 100 may include multiple pulse generators, similar to pulse generator 174, where each pulse generator is coupled to one or more electrodes and controlled by the microcontroller 164 to deliver select stimulus pulse(s) to the corresponding one or more electrodes.

Microcontroller 164 is illustrated to include a CRT control circuitry 166 to control the timing of the stimulation pulses (e.g., pacing rate, atrio-ventricular (AV) delay, atrial interconduction (A-A) delay, or ventricular interconduction (V-V) delay, etc.). The timing control circuitry 166 may also be used for the timing of refractory periods, blanking intervals, noise detection windows, evoked response windows, alert intervals, marker channel timing, and so on. Microcontroller 164 also has an arrhythmia detector 168 for detecting arrhythmia conditions and a morphology detector 170 to review and analyze one or more features of the morphology of cardiac signals. The microcontroller 164 also includes a morphology and conduction pattern (MCP) detector 170 and a template manager 171 that are described below in more detail. Although not shown, the microcontroller 164 may further include other dedicated circuitry and/or firmware/software components that assist in monitoring various conditions of the patient's heart and managing pacing therapies.

The IMD 100 includes sensing circuitry 180 selectively coupled to one or more electrodes that perform sensing operations, through the switch 192 to detect the presence of cardiac activity in the right chambers of the heart. The sensing circuitry 180 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 192 determines the sensing polarity of the cardiac signal by selectively closing the appropriate switches. In this way, the clinician may program the sensing polarity independent of the stimulation polarity.

The output of the sensing circuitry 180 is connected to the microcontroller 164 which, in turn, triggers or inhibits the pulse generator 174 in response to the absence or presence of cardiac activity. The sensing circuitry 180 receives a control signal 178 from the microcontroller 164 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 180 is illustrated. Optionally, the IMD 100 may include multiple sensing circuit, similar to sensing circuit 180, where each sensing circuit is coupled to one or more electrodes and controlled by the microcontroller 164 to sense electrical activity detected at the corresponding one or more electrodes. The sensing circuit 180 may operate in a unipolar sensing configuration or in a bipolar sensing configuration.

The IMD 100 further includes an analog-to-digital (ND) data acquisition system (DAS) 190 coupled to one or more electrodes via the switch 192 to sample cardiac signals across any pair of desired electrodes. The data acquisition system 190 is configured to acquire intracardiac electrogram signals, convert the raw analog data into digital data, and store the digital data for later processing and/or telemetric transmission to an external device 104 (e.g., a programmer, local transceiver, or a diagnostic system analyzer). The data acquisition system 190 is controlled by a control signal 188 from the microcontroller 164.

The microcontroller 164 is coupled to a memory 152 by a suitable data/address bus 162. The programmable operating parameters used by the microcontroller 164 are stored in memory 152 and used to customize the operation of the IMD 100 to suit the needs of a particular patient. CRT and operating parameters define, for example, paced event amplitude, pulse duration, electrode polarity, rate, sensitivity, automatic features, arrhythmia detection criteria, and the amplitude, wave shape and vector of each shocking pulse to be delivered to the patient's heart. The operating parameters of the IMD 100 may be non-invasively programmed into the memory 152 through a telemetry circuit 154 in telemetric communication via communication link 150 (e.g., MICS, Bluetooth, or other link) with the external device 104. The telemetry circuit 154 allows intracardiac electrograms and status information relating to the operation of the IMD 100 (as contained in the microcontroller 164 or memory 152) to be sent to the external device 104 through the established communication link 150. The memory 152 also stores morphology templates 151 and conduction pattern templates 153 that are used in accordance with embodiments herein to identify and label pseudo-fusion.

The IMD 100 can further include one or more physiologic sensors 156. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Signals generated by the physiological sensors 156 are passed to the microcontroller 164 for analysis. While shown as being included within the unit 100, the physiologic sensor(s) 156 may be external to the IMD 100, yet still be implanted within or carried by the patient. Examples of physiologic sensors might include sensors that, for example, sense respiration rate, pH of blood, ventricular gradient, activity, position/posture, minute ventilation (MV), and so forth.

A battery 158 provides operating power to all of the components in the IMD 100. The battery 158 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the IMD 100 employs lithium/silver vanadium oxide batteries.

The IMD 100 further includes an impedance measuring circuit 160, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 160 is coupled to the switch 192 so that any desired electrode may be used.

The microcontroller 164 further controls a shocking circuit 184 by way of a control signal 186. The shocking circuit 180 generates shocking pulses of low (e.g., up to 0.5 joules), moderate (e.g., 0.5-10 joules), or high energy (e.g., 11 to 40 joules), as controlled by the microcontroller 164. Such shocking pulses are applied to the patient's heart through shocking electrodes. It is noted that the shock therapy circuitry is optional and may not be implemented in the IMD 100, as the various slave pacing units described below will typically not be configured to deliver high voltage shock pulses.

Process to Label Pseudo-Fusion

The microcontroller 164 includes a template manager 171 that operates as described herein to generate sets of templates that are used to distinguish pseudo-fusion pacing from effective pacing that captures the heart. To build templates, the template manager 171 cycles through multiple CRT parameters that define different corresponding stimulation pulses. During one cycle, a stimulation pulse is delivered based on a first set of CRT parameters. For example, the first set of CRT parameters may define "right ventricular only pacing". The first set of CRT parameters may be used to deliver one or more stimulation pulses to the RV-only, while the LV is not paced, during one or more corresponding cardiac cycles. Following each stimulation pulse, a baseline cardiac signal is sensed during the corresponding cardiac cycle. The first set of CRT parameters may be used during multiple cardiac cycles, during which corresponding baseline cardiac signals are sensed.

Once a desired amount of cardiac signals are collected in connection with RV-only pacing using the first set of CRT parameters, the template manager 171 switches to a different type of stimulation pulse, such as "LV-only pacing", while the RV is not paced. The LV-only pacing is defined by a second set of CRT parameters. LV-only pacing is utilized during one or more cardiac cycles. During each LV-only pacing cardiac cycle, corresponding baseline cardiac signals are sensed and collected. The second set of CRT parameters are utilized during a desired number of cardiac cycles until a desired amount of corresponding baseline cardiac signals are collected. Thereafter, the template manager 171 switches to a third set of CRT parameters that define a different stimulation therapy, such as biventricular (BiV) pacing. BiV baseline cardiac signals are sensed and collected during one or more cardiac cycles while the third set of CRT parameters are utilized to deliver biventricular pacing.

Additionally or alternatively, the template manager 171 may designate one group of cardiac cycles, for which "no-pacing" baseline cardiac signals are sensed, wherein no CRT stimulation is delivered. When no-pacing baseline cardiac signals are sensed with no CRT stimulation, the corresponding depolarization wave front propagates in connection with intrinsic conduction based on intrinsic atrial events.

The template manager 171 collects baseline cardiac signals along multiple sensing vectors that utilize an RV electrode and multiple MSLV electrodes. For example, the sensing vectors may comprise a sensing vector between an RV electrode and the housing/can of the IMD, and/or between an RV electrode and a coil electrode (e.g., an SVC coil) (referred to as "RV-Can/Coil"). The sensing vectors may comprise a sensing vector between a distal LV electrode (LVD1) and the housing/can of the IMD and/or a coil electrode (referred to as "LVD1-Can/Coil"). A sensing vector may be between a first mid-LV electrode (LVM2) and the housing/can of the IMD and/or a coil electrode (referred to as "LVM2-Can/Coil"). A sensing vector may be between a second mid-LV electrode (LVM3) and the housing/can of the IMD and/or a coil electrode (hereafter referred to as "LVM3-Can/Coil"). A sensing vector may be between a proximal electrode (LVP4) and the housing/can of the IMD and/or a coil electrode (referred to as "LVP4-Can/Coil").

In the foregoing example, four separate LV sensing vectors are utilized to collect four separate baseline cardiac signals in connection with a single cardiac cycle (and an associated single paced event). When the same type of stimulus (e.g., biventricular pacing) is delivered multiple times, a corresponding number of groups of four separate baseline cardiac signals are collected. For example, when BiV pacing is delivered during 4 cardiac cycles and 4 sensing LV vectors are used, 16 separate baseline cardiac signals are collected. When multiple baseline cardiac signals are collected along an individual sensing vector in connection with a single type of stimulus therapy, the multiple baseline cardiac signals may be combined to form a combined baseline cardiac signal (e.g., determining the average, mean, etc.).

Each type of event (intrinsic or paced) has a corresponding unique electrical signature comprised of (a) an LV conduction pattern and (b) a collection of LV EGM morphologies. The template manager 171 analyzes the baseline cardiac signals to generate templates related to the electrical signatures. The templates include morphology templates and/or conduction pattern templates, and the templates are associated with particular types of stimulation, such as RV-only, LV-only, BiV, or no-pace. For example, a BiV morphology template may be formed based on baseline cardiac signals sensed over the separate sensing vectors in connection with delivering biventricular stimulation. As another example, a BiV conduction pattern template is formed by the template manager 171 based on the BiV baseline cardiac signals from the various sensing vectors. As another example, an RV-only morphology template and an RV-only conduction pattern template are generated based on baseline cardiac signals sensed over the various sensing vectors in connection with delivering RV-only pacing. Similarly, an LV-only morphology template, LV-only conduction pattern template, no-pacing (intrinsic) morphology template and no-pacing conduction pattern template are formed by the template manager 171. The template manager 171 stores the morphology and conduction pattern templates as sets of templates in the memory 152. For example, morphology templates 151 and conduction pattern templates 153 may be stored separately or together.

FIGS. 3A-3D illustrate examples of conduction pattern templates that may be generated by the template manager 171 in accordance with embodiments herein. FIGS. 4A-4D illustrate examples of morphology templates that may be generated by the template manager 171 in accordance with embodiments herein.

Figure 3A:
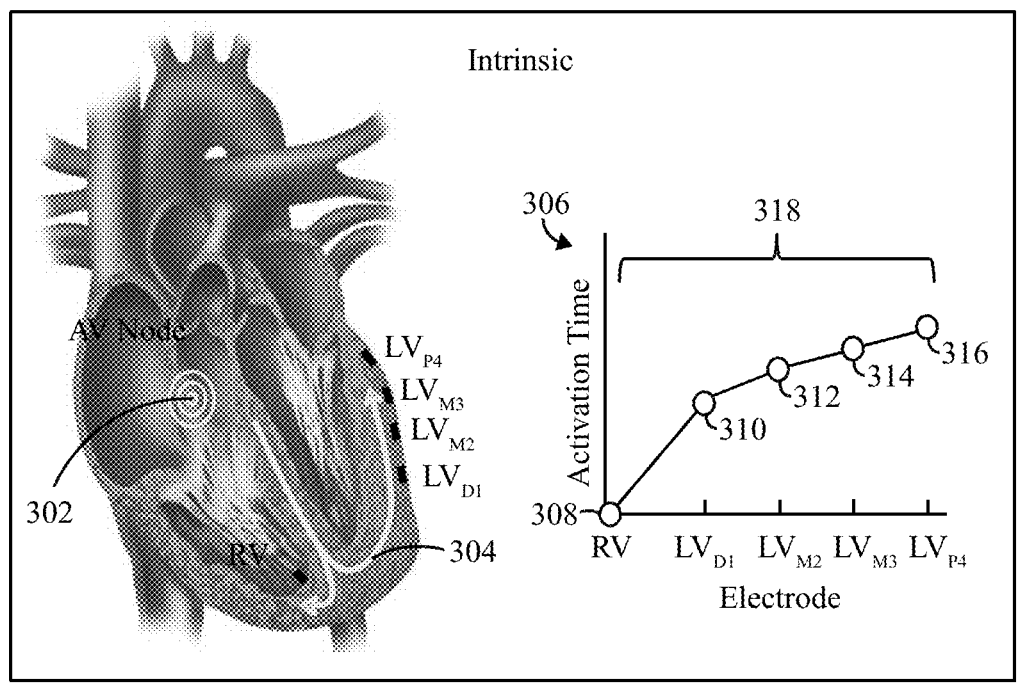
FIG. 3A illustrates a graphic representation of the heart along with an example direction in which a depolarization wave front propagates in response to an intrinsic no-pace event.

FIG. 3A illustrates a graphic representation of the heart along with an example direction in which a depolarization wave front propagates in response to an intrinsic no-pace event. An intrinsic event occurs at the AV node 302, after which a depolarization wave front propagates in the directions indicated by arrow 304. The wave front travels from the AV node to the ventricles along the bundle of HIS, separating into left and right bundle branches, and then traveling to the Purkinje fibers. The graph 306 illustrates a conduction pattern with activation time along the vertical axis and the sensing electrode site along the horizontal axis. During normal intrinsic behavior, the depolarization wave front originates at the SA node and propagates along the natural, Purkinje pathway. The depolarization wave front first passes the RV electrode (denoted in FIG. 3A as activation time 308). The depolarization wave front progresses along the path illustrated by the arrow 304 along the wall of the LV traveling from apex-to-base and from endocardium-to-epicardium. In connection there with, the depolarization wave front is detected at the LVD1 electrode at activation time 310, the LVM2 electrode at activation time 312, the LVM3 electrode activation time 314 and the LVP4 electrode at activation time 316, thereby forming the conduction pattern template 318. In the example of FIG. 3A, the template manager 171 generates the intrinsic conduction pattern template 318 by defining activation timing and an LV electrode activation order. The conduction pattern template 318 defines LV activation times that are associated with an RV-to-LVD1 activation interval, an RV-to-LVM2 activation interval, an RV-to-LVM3 activation interval, and an RV-to-LVP4 activation interval. The activation timing and LV electrode activation order indicate a corresponding stimulus origin at the AV node.

Figure 3B:
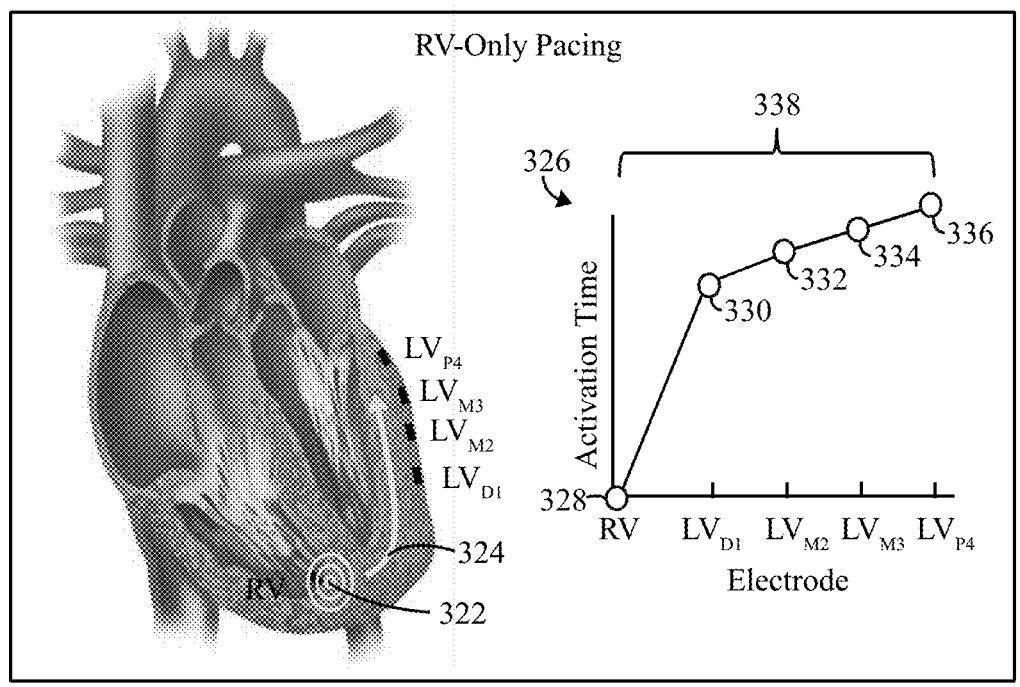
FIG. 3B illustrates a graphic representation of the heart along with an example direction in which a depolarization wave front propagates in response to an RV-only pacing event.

FIG. 3B illustrates a graphic representation of the heart along with an example direction in which a depolarization wave front propagates in response to an RV-only pacing event. An RV-only pacing event is delivered at the RV pacing site 322, after which a depolarization wave front propagates in the direction indicated by arrow 324. The wave front travels from the RV pacing site 322 along the right bundle branch and Purkinje fibers. The graph 326 illustrates an RV-only conduction pattern 338 with activation time along the vertical axis and the sensing electrode site along the horizontal axis. The depolarization wave front is detected at the LVD1 electrode at activation time 330, the LVM2 electrode at activation time 332, the LVM3 electrode activation time 334 and the LVP4 electrode at activation time 336, thereby forming the conduction pattern template 338. In the example of FIG. 3B, the template manager 171 generates the LV conduction pattern template 338 by determining activation timing and an LV electrode activation order that indicates a corresponding stimulus origin at an RV pacing site. The template manager 171 determines LV activation times that are associated with an RV-to-LVD1 activation interval, an RV-to-LVM2 activation interval, an RV-to-LVM3 activation interval, and an RV-to-LVP4 activation interval.

Due to the apical location of most RV leads, a wave front originating from RV-only pacing may exhibit similar LV electrode conduction patterns as an intrinsic depolarization wave front. For example, in FIG. 3B, the depolarization wave front progresses along the path illustrated by the arrow 324 along the wall of the LV traveling from apex-to-base and from endocardium-to-epicardium in a manner similar to the depolarization wave front of FIG. 3A (related to an intrinsic beat). However, the activation timing (328 to 330) between the RV paced event and sensing the depolarization wave front at the LVD1 electrode differs (e.g., is longer) than the activation timing (308 to 310) between an intrinsic depolarization wave front at the RV electrode and LVD1 electrode in FIG. 3A.

Figure 3C:
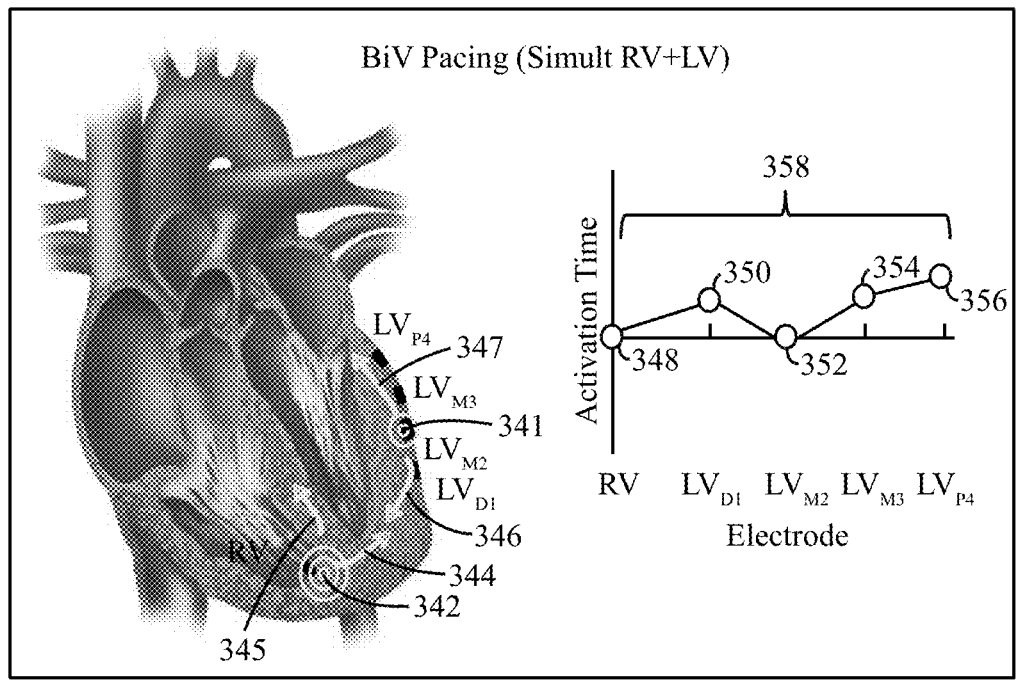
FIG. 3C illustrates a graphic representation of the heart along with an example direction in which a depolarization wave front propagates in response to an biventricular (BiV) pacing event.

FIG. 3C illustrates a graphic representation of the heart along with an example direction in which a depolarization wave front propagates in response to a biventricular (BiV) pacing event. A BiV pacing event is delivered at an RV pacing site 342 and an LVM2 pacing site 341, after which depolarization wave fronts propagate in the directions indicated by arrows 344-347. For example, an RV originated depolarization wave front propagates in the directions of arrows 344-345, while an LVM2 originated depolarization wave front propagates in the directions of arrows 346-347.

The RV originated depolarization wave front (arrows 344-345) travels from the RV pacing site 342 along the right bundle branch and may travel along the bundle of HIS (if not already depolarized). The LVM2 originated depolarization wave front (arrows 346-347) propagates in opposite directions from the LVM2 electrode along the right bundle branch. Ultimately the RV originated and LVM2 originated depolarization wave fronts meet one another along the right bundle branch to yield a conduction pattern template 358 having activation times 348-356. The activation times 348 and 352 are illustrated to occur at approximately the same time, in accordance with an example where the RV pacing site and LVM2 pacing site are stimulated simultaneously.

Optionally, a programmed delay may be introduced between the times at which the RV and LVM2 pacing sites are stimulated. Following the paced events at the RV and LVM2 electrodes, the depolarization wave fronts are sensed at the LVD1, LVM3 and LVP4 electrodes at the activation times 350, 354 and 356, respectively. Notably, the depolarization wave front is sensed at approximately the same time at the LVD1 and LVM3 electrodes. Accordingly, the conduction pattern template 358 exhibits noted differences from the activation timing and activation electrode order in the conduction pattern templates for an intrinsic beat and an RV-only paced beat. The conduction pattern template 358 defines LV activation times that are associated with an RV-to-LVD1 activation interval, an RV-to-LVM2 activation interval, an RV-to-LVM3 activation interval, and an RV-to-LVP4 activation interval. The wave front behavior and template 358 of FIG. 3C represents an effective captured beat where the wave fronts provide effective CRT pacing.

Figure 3D:
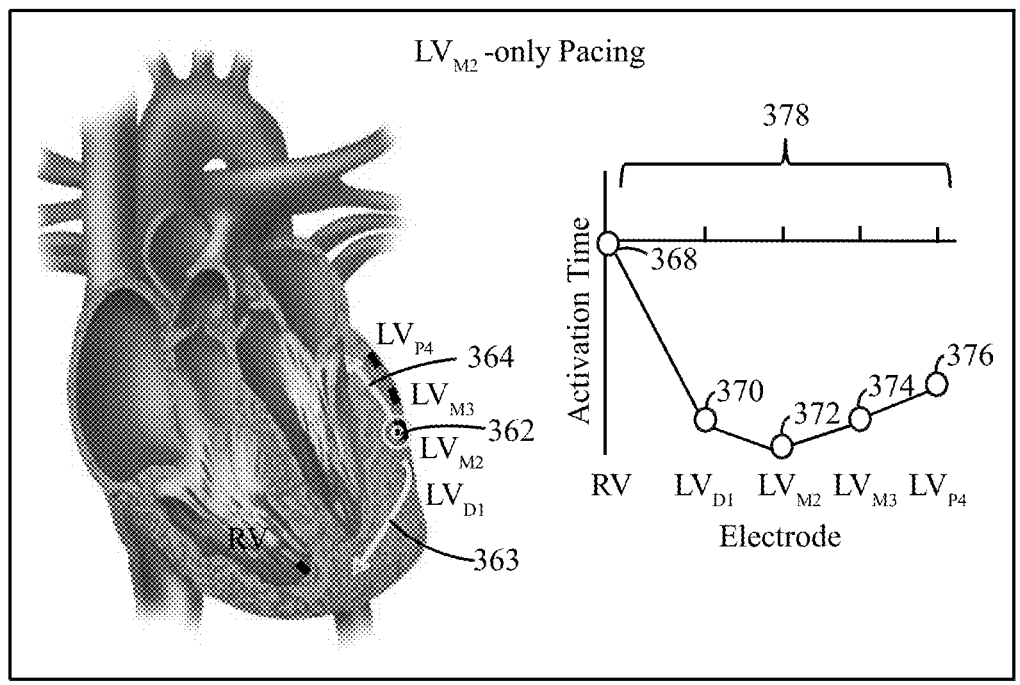
FIG. 3D illustrates a graphic representation of the heart along with an example direction in which a depolarization wave front propagates in response to an LVM2-only pacing event.

FIG. 3D illustrates a graphic representation of the heart along with an example direction in which a depolarization wave front propagates in response to an LVM2-only pacing event. A LVM2-only pacing event is delivered at an LVM2 pacing site 362, after which depolarization wave fronts propagate in the directions indicated by arrows 363-364. For example, the LVM2 originated depolarization wave fronts (arrows 363-364) propagate in opposite directions from the LVM2 electrode along the right bundle branch. The LVM2 originated depolarization wave fronts generates a conduction pattern template 378 having activation times 368-376 for the RV, LVD1, LVM2, LVM3 and LVP4 electrodes, respectively. The conduction pattern template 378 has a first activation time 372 at the LVM2 electrode where the paced event was delivered, followed by similar activation times 370, 374 at the LVD1 and LVM3 electrodes, followed by an activation time 376 at the LVP4 electrode. Ultimately, the last activation time 368 occurs at the RV electrode. In the foregoing examples, the LV paced events are shown to originate at the LVM2 electrode. Optionally, additional or alternative LV electrodes may be used as the pacing site.

As illustrated in connection with FIGS. 3A-3D, at least BiV pacing or LV-only pacing, when effective, result in entirely different activation times and orders, as compared to an intrinsic event or an RV-only pacing event. FIGS. 3A-3D illustrate depolarization wave fronts and corresponding conduction patterns, during which no pseudo-fusion is experienced with an intrinsically originated depolarization wave front. However, when pseudo-fusion occurs between an intrinsically originated depolarization wave front and one or more of the depolarization wave fronts illustrated in FIGS. 3A-3D, the resulting conduction pattern will differ from the conduction pattern templates 318, 338, 358 and 378.

Figure 3E:
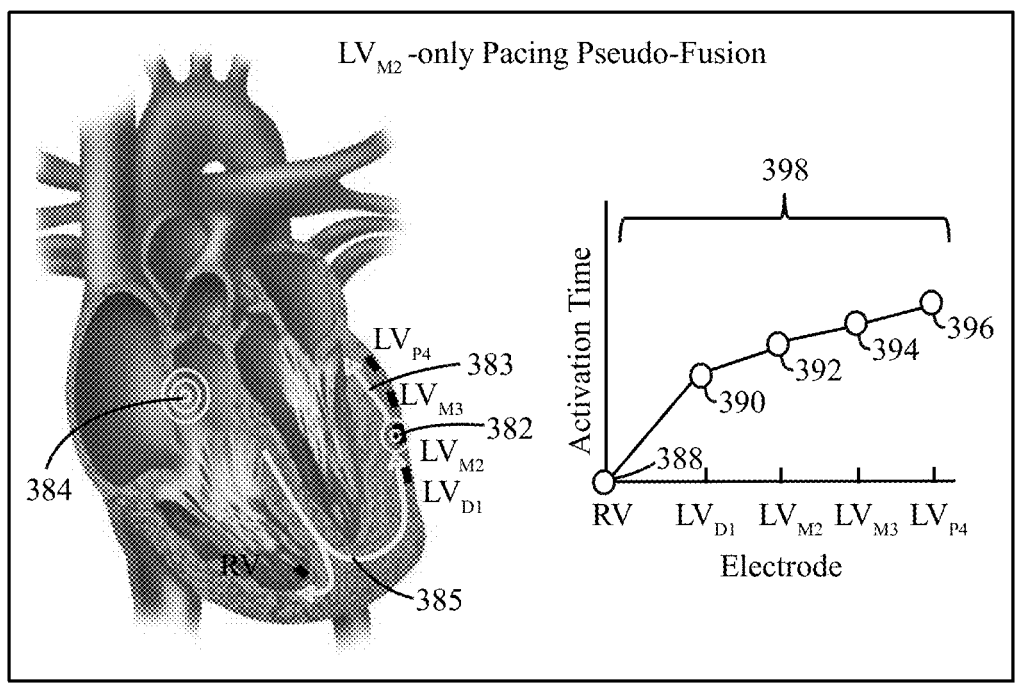
FIG. 3E illustrates a graphical representation of the heart along with an example in which an LVM2-only pacing event experiences pseudo-fusion with an intrinsically originated depolarization wave front.

FIG. 3E illustrates a graphical representation of the heart along with an example in which an LVM2-only pacing event experiences pseudo-fusion with an intrinsically originated depolarization wave front. An LVM2 only pacing event is delivered at the LVM2 pacing site 382, in response to which a depolarization wave front propagates in the direction indicated by arrow 383. Separately, an intrinsic event 384 occurs at the AV node, in response to which a depolarization wave front propagates in the direction of arrows 385. The intrinsically originated depolarization wave front travels along the bundle of HIS and branches along the left and right bundle branches. The LVM2 originated depolarization wave front travels along the right bundle branch upward from the LVM2 pacing site 382. Due to the relative timing of the intrinsic event 384 and the time at which the LVM2-only paced event was delivered, the depolarization wave fronts are combined in a pseudo-fused manner that is ineffective.

The pseudo-fused depolarization wave fronts form a conduction pattern 398 (detected by the MCP detector 170 in FIG. 2) having activation times 388-396. In the conduction pattern 398, the RV and LVD1 electrodes sense the depolarization wave front (associated with arrow 385) first (at activation times 388 and 390), before delivery of the LVM2-only pacing event at activation time 392. Thereafter, the LVM3 and LVP4 electrodes sense the depolarization wave front (associated with arrow 383) at activation times 394 and 396.

In accordance with embodiments herein, the MCP detector 170 identifies and compares the conduction pattern 398 to the conduction pattern templates 318, 338, 358 and 378. An LVM2-only pacing event would be expected to exhibit a conduction pattern similar to the conduction pattern template 378. In the example of FIG. 3E, the MCP detector 170 determines that the conduction pattern 398 does not resemble the corresponding template 378. Instead, the MCP detector 170 determines that the conduction pattern 398 resembles the intrinsic conduction pattern template 318. Based on the comparison between the conduction pattern 398 and the templates 318, 378, alone or in combination with additional information, the MCP detector 170 declares the event to represent pseudo-fusion.

Figure 4A:
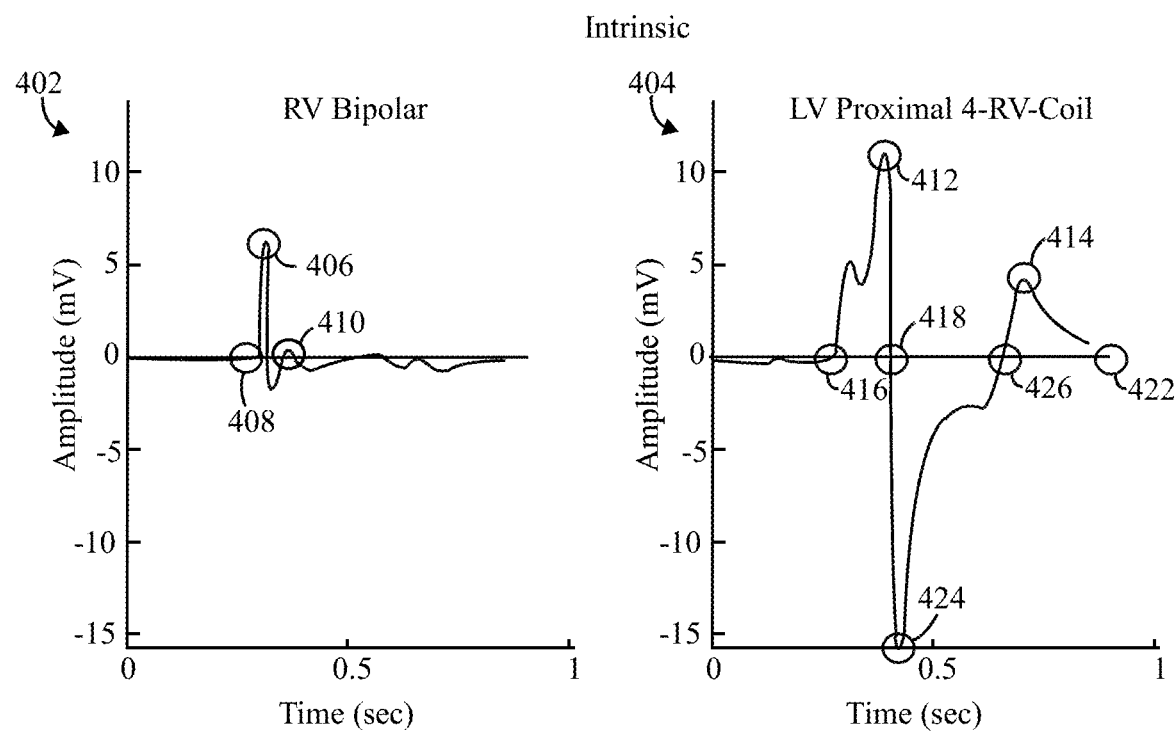
FIG. 4A illustrates example morphology templates generated by the template manager in accordance with embodiments herein.

As explained herein, the sensed cardiac signals exhibit different EGM morphologies that are unique to different stimulus origins. FIG. 4A illustrates example morphology templates generated by the template manager 171 in accordance with embodiments herein. The morphology templates of FIG. 4A include an RV bipolar morphology template 402 and an LVP4-RV Coil morphology template 404. The RV bipolar morphology template 402 defines one or more characteristics of interest concerning the shape and/or timing of the cardiac signal sensed along an RV-tip to RV-ring bipolar sensing vector over one cardiac cycle that originated from an intrinsic event. The LVP4-RV Coil morphology template 404 defines one or more characteristics of interest concerning the shape and/or timing of the cardiac signal sensed along a LVP4 to RV coil sensing vector over the same cardiac cycle that originated from the same intrinsic event as the RV bipolar morphology template 402. For example, the characteristics of interest may represent the peaks, zero crossing and/or valleys of the sensed cardiac signals. In the morphology templates 402 and 404, the characteristics of interest are indicated by peaks 406, 412, and 414 and by zero crossings 408, 410, and 416-422, and by valley 424. The characteristics of interest may be defined by an amplitude and timing. Additionally or alternatively, the characteristics of interest may be defined by a slope and positive/negative property of the slope (e.g., at the zero crossings).

Optionally, the morphology templates 422, 424 (and any other morphology templates) may be defined by triangles. For example, the microcontroller 164 may analyze the shape of the cardiac signals to define triangles 490-492. The triangles 490-492 have vertices at the peaks, zero crossings and valleys 434-439. The triangles from templates and candidate beats are compared for matches.

Figure 4B:
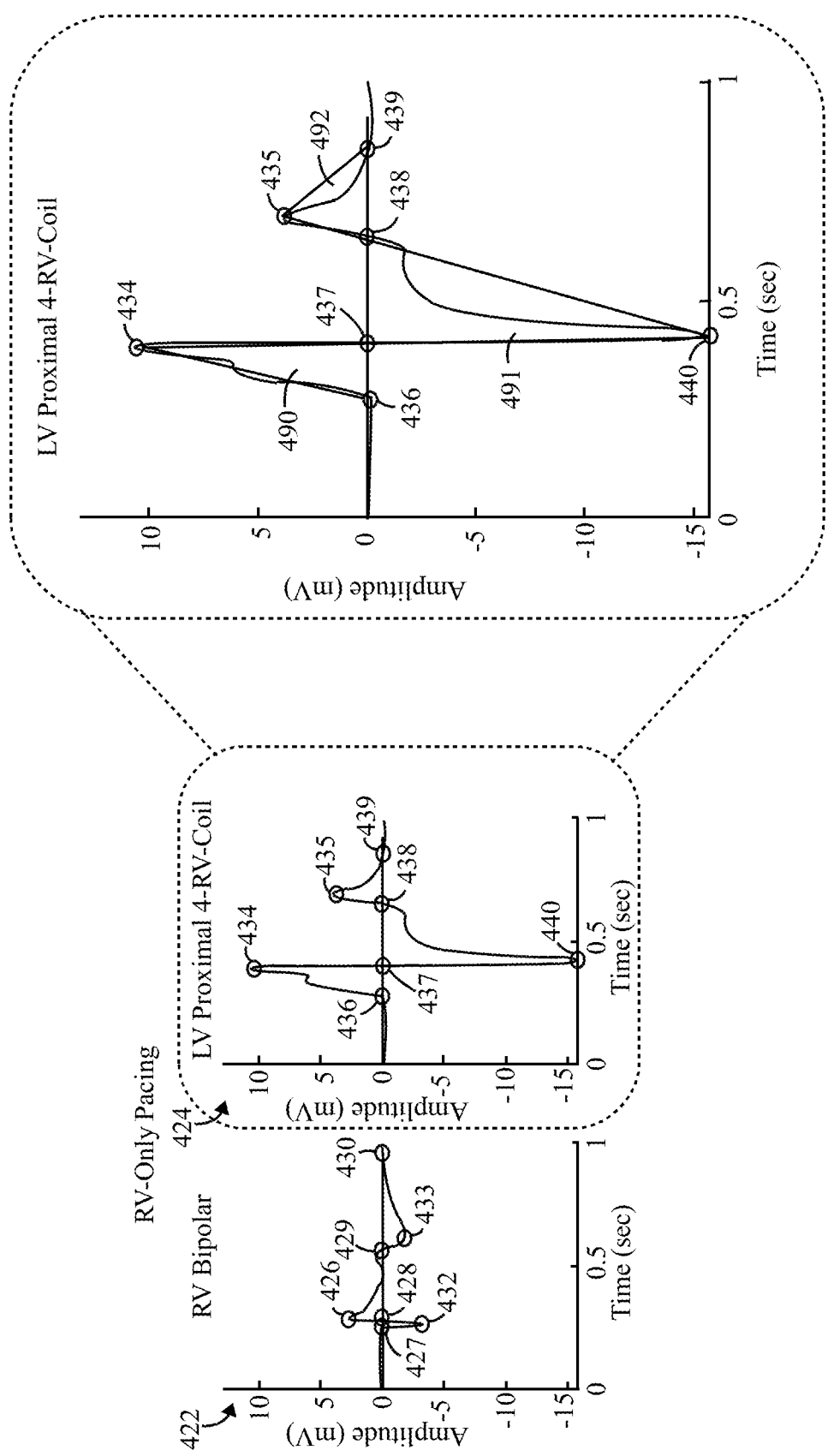
FIG. 4B illustrates example morphology templates that are sensed in connection with an RV-only pacing event.

FIG. 4B illustrates example morphology templates 422, 424 that are sensed in connection with an RV-only pacing event. The morphology template 422 is generated from cardiac signals sensed along the RV tip to RV ring bipolar sensing vector. The morphology template 424 is generated from cardiac signals sensed along the LVP4 to RV coil sensing vector. The morphology templates 422, 424 are generated from cardiac signals sensed during a single common cardiac cycle in which RV-only pacing was delivered. The morphology template 422 is defined by characteristics of interest that include a peak 426, zero crossings 427-433, and valleys 432 433. The morphology template 424 is defined by characteristics of interest that include peaks 434-435, zero crossings 436-439, and valley 440.

Figure 4C:
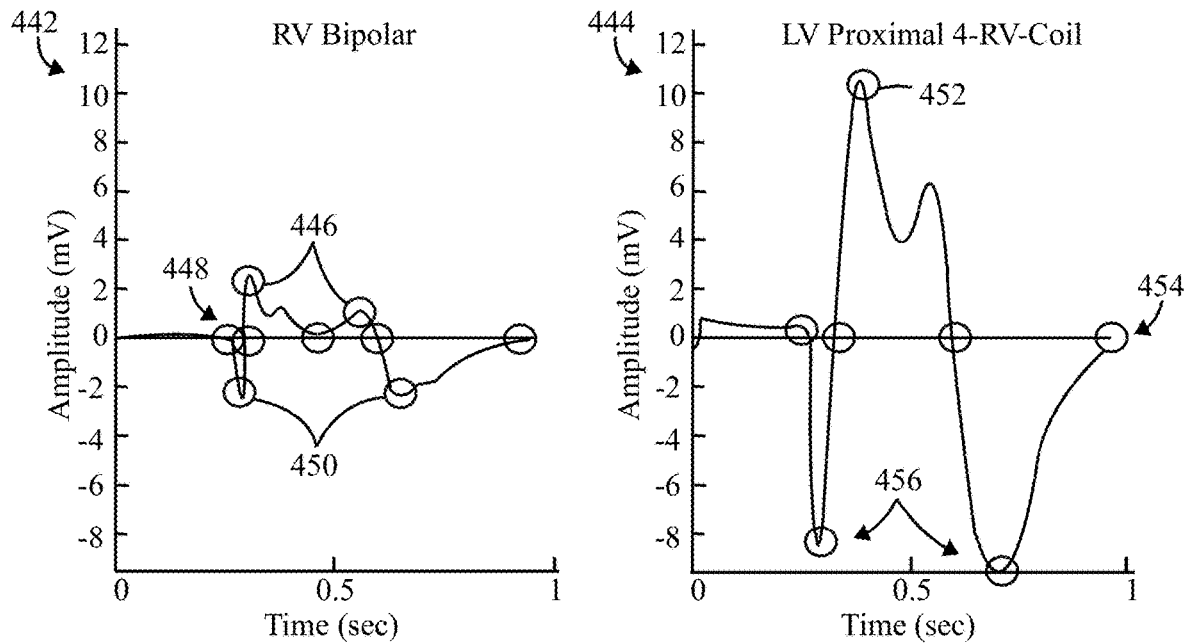
FIG. 4C illustrates example morphology templates that are sensed in connection with a BiV pacing event.

FIG. 4C illustrates example morphology templates 442, 444 that are sensed in connection with a BiV pacing event. The morphology template 442 is generated from cardiac signals sensed along the RV tip to RV ring bipolar sensing vector. The morphology template 444 is generated from cardiac signals sensed along the LVP4 to RV coil sensing vector. The morphology templates 442, 444 are generated from cardiac signals sensed during a single common cardiac cycle in which biventricular pacing was delivered. The morphology template 442 is defined by characteristics of interest that include peaks 446, zero-crossings 448 and valleys 450. The morphology template 444 is defined by characteristics of interest that include a peak 452, zero crossings 454 and valleys 456.

Figure 4D:
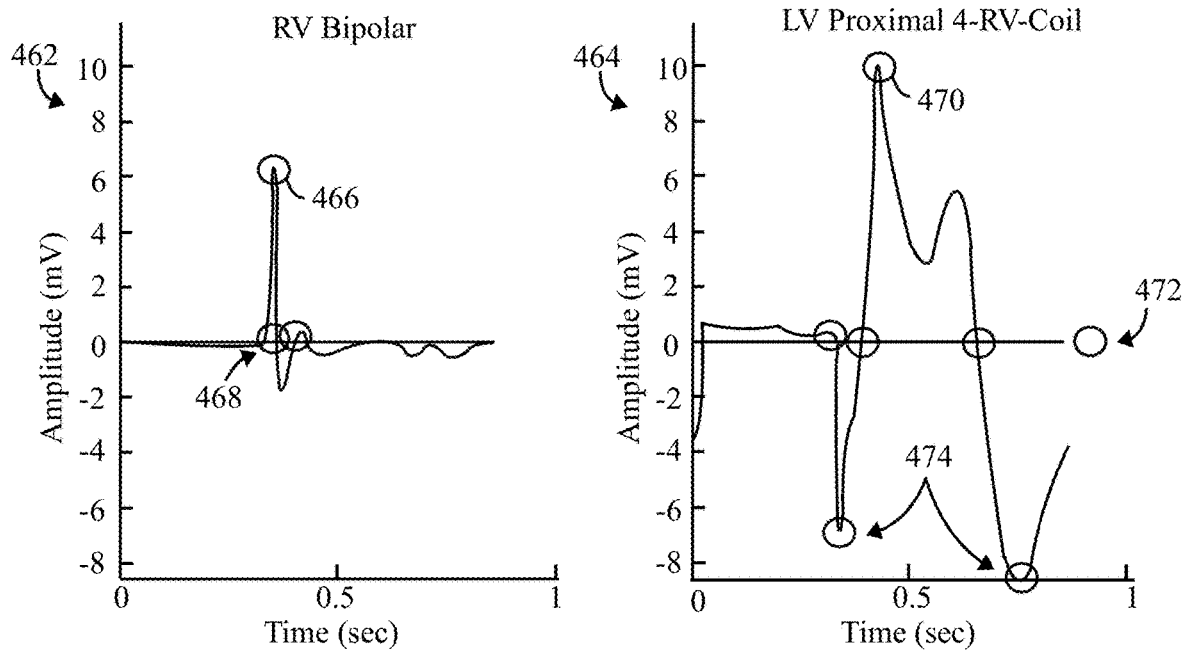
FIG. 4D illustrates example morphology templates that are sensed in connection with an LV-only pacing event at the LVP4 electrode.

FIG. 4D illustrates example morphology templates 462, 464 that are sensed in connection with an LV-only pacing event at the LVP4 electrode. The morphology template 462 is generated from cardiac signals sensed along the RV tip to RV ring bipolar sensing vector. The morphology template 464 is generated from cardiac signals sensed along the LVP4 to RV coil sensing vector. The morphology templates 462, 464 are generated from cardiac signals sensed during a single common cardiac cycle in which an LV-only pacing event was delivered at the LVP4 electrode. The morphology template 462 is defined by characteristics of interest that include a peak 466, and zero-crossings 468. The morphology template 464 is defined by characteristics of interest that include a peak 470, zero crossings 472 and valleys 474.

As shown in FIGS. 4A-4D, the RV morphology templates may include only positive spikes when the RV is not paced (FIG. 4A, 4D), but the RV morphology templates may have a negative-positive-negative tri-phasic morphology when RV is effectively paced (FIG. 4B, 4C). Furthermore, the LV morphology templates have a positive-negative-positive morphology when not paced (FIG. 4A, 4B), but have a negative-positive-negative morphology when effectively paced (FIG. 4C, 4D). Although example morphologies are not shown for LV pseudo-fusion pacing, by way of example a morphology for an LV pseudo-fusion event may resemble an intrinsic morphology or an RV-only pacing morphology. The morphology for an LV pseudo-fusion event would not resemble the morphology for an LV paced event in either BiV or LV-only pacing. Hence, during BiV or LV-only paced events, the expected morphology should not resemble an intrinsic or VR-only pacing morphology.

FIGS. 4A-4D illustrates morphology templates in connection with 2 sensing vectors. Additionally or alternatively, morphology templates may be generated in connection with other sensing vectors. For example, morphology templates may be generated in connection with sensing vectors between any or all of the LV electrodes (e.g., LVP4, LVM3, LVM2, LVD1) and any or all of the RV electrodes (e.g., RV coil, RV tip, RV ring).

Figure 5:
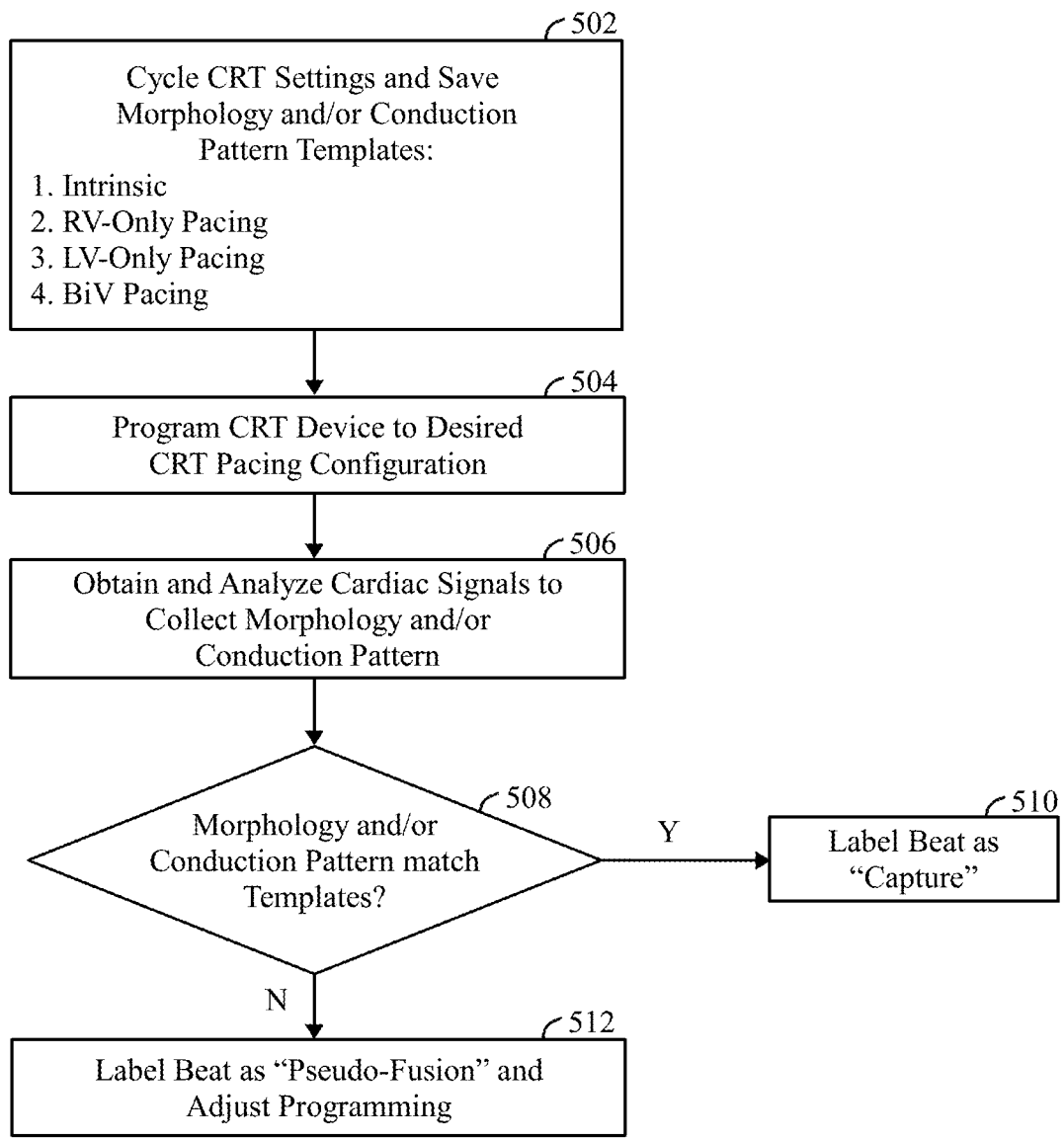
FIG. 5 illustrates a method for distinguishing LV pseudo-fusion pacing from normal/effective LV pacing in accordance with embodiments herein.

FIG. 5 illustrates a method for distinguishing LV pseudo-fusion pacing from normal/effective LV pacing in accordance with embodiments herein. At 502, one or more processors of the IMD (or an external device) generate sets of templates, where each set of templates corresponds to a select type of stimulation, namely 1) Intrinsic conduction; 2) RV-only pacing; 3) LV-only pacing using the programmed LV pulse configuration and 4) BiV pacing using the programmed LV pulse configuration. The templates are generated based on averages for the information of interest from multiple cardiac beats. For example, the conduction pattern templates may comprise mean LV activation times, such as a minimum time for a change in voltage or a unit of time (e.g., dV/dtmin), associated with the 4 LV electrodes. The LV activation times may be relative to an RV activation time and may be based on a select number beats (e.g., 10+). The LV activation times may be associated with an RV-to-LVD1 activation interval, an RV-to-LVM2 activation interval, an RV-to-LVM3 activation interval, and an RV-to-LVP4 activation interval. By way of example the mean LV activation times for the various LV electrodes may be LVD1=100 ms, LVM2=110 ms, LVM3=115 ms, and LVP4=125 ms. For device-based computational feasibility, the 4 RV-to-LV activation times can be determined using 4 sequential beats, during which a consistent conduction pattern can be assumed. In this manner, RV-to-LVD1, RV-to-LVM2, RV-to-LVM3, and RV-to-LVP4 activation intervals can be determined from sequential beats in series to characterize the same conduction pattern.

The morphology templates may be unipolar or far-field EGM morphology templates for sensing vectors that include the select electrodes (e.g., RV-Can/Coil, LVD1-Can/Coil, LVM2-Can/Coil, LVM3-Can/Coil, LVP4-Can/Coil). The morphology templates can be established either in-clinic or periodically by the IMD by adjusting AV and VV timing to manage a stimulus origin associated with each template. For example, the IMD may be programmed to a high pacing rate, to have a short AV delay, and/or a CRT feature may be turned off, such as to establish an RV-only template. The morphology templates store characteristics of interest (e.g., related to positive deflection local maximums (peaks), negative deflection local minimums (valleys), and zero crossings) as an amplitude and time relative to a reference time-point (e.g., RV activation). The set of templates may comprise a set of morphology templates that include characteristics of interest from cardiac signals for multiple beats, the characteristics of interest including amplitudes of positive deflection local maximums, negative deflection local minimums, and zero crossings. The characteristics of interest may further include characteristic timings with respect to a reference time-point (e.g., the RV activation time).

The characteristics of interest (e.g., peaks, zero crossings, valleys) provide a limited amount of data that can be used to reconstruct an EGM waveform. Optionally, the characteristics of interest can be simplified into triangular representations of segments of an EGM waveform (FIG. 4B). The triangular representations can be computationally efficient when comparing new candidate cardiac cycles to the morphology templates (e.g., simplified, numerical cross-correlation). Again, for device based computational feasibility, the EGM waveform for each candidate cardiac cycle for each LV lead can be characterized from sequential beats in series, rather than simultaneously. The templates can be established using relatively short AVD, short VVD, and sufficient pacing amplitudes to reasonably guarantee capture, or lack thereof, for each of the 4 stimulus types. Templates can be established either in-clinic at the time of implant, or out-of-clinic periodically by the IMD itself. Once the templates are established, flow moves to 504.

At 504, the one or more processors of the IMD 100 load a set of CRT program parameters in order to program the IMD to implement pacing in accordance with the desired pacing configuration. For example, the CRT program parameters may be loaded by a clinician during and in clinic visit, downloaded by a home patient monitoring system, downloaded from a medical network through an external device operated by a patient (e.g., smart phone, tablet device) and the like. The IMD 100 begins delivering the pacing configuration that includes LV pacing, such as LV only pacing or biventricular pacing.

At 506, the one or more processors of the IMD 100 obtain cardiac signals, associated with a candidate beat, from the MSLV electrodes distributed along a left ventricle. The one or more processors analyze the cardiac signals to collect at least one of an MSLV conduction pattern or an MSLV morphology for the corresponding candidate beat. Optionally, the operation at 506 may be conducted in connection with multiple candidate beats that are combined before determining the MSLV conduction pattern and/or MSLV morphology. Additionally or alternatively, at 506, multiple MSLV morphologies and conduction patterns may be determined (in connection with the corresponding multiple beats) to be subsequently analyzed separately and/or combined to form a mean or average MSLV conduction pattern or morphology.

At 508, the one or more processors compare the MSLV morphologies and/or conduction patterns to one or more associated templates. For example, the MSLV morphology for a candidate beat may be compared to a set of MSLV morphology templates, where each template within the set corresponds to a different type of stimulation (e.g., intrinsic, RV-only, LV only and BiV). Similarly, the MSLV conduction pattern for the candidate beat may be compared to a set of MSLV conduction templates, where each template within a set corresponds to a different type of stimulation. For example, when the pacing configuration represents LV only pacing, the comparison at 508 would expect the MSLV morphology and conduction pattern for the candidate beat to match the LV only morphology and conduction pattern templates. Alternatively, when the pacing configuration represents BiV pacing, the comparison at 508 would expect the MSLV morphology and conduction pattern for the candidate beat to match the BiV morphology and conduction pattern templates. As explained above, when pseudo-fusion is present, a candidate beat may exhibit an MSLV morphology and/or conduction pattern that resembles intrinsic and/or RV-only morphology and/or conduction pattern templates.

Optionally, at 508, the one or more processors may apply a weighted comparison to the various templates. For example, when certain types of templates are expected to be better indicators of pseudo-fusion, a weight may be increased for comparison results between the corresponding types of templates and candidate beats. For example, in connection with certain types of CRT therapy, conduction patterns may be a better indicator of pseudo-fusion than morphologies. Accordingly, matches or differences between conduction pattern templates and candidate beats may be afforded a greater weight than matches/differences between morphology templates and candidate beats. Alternatively, in connection with other types of CRT therapies, morphologies may exhibit better indicators of perfusion.

Based on the comparison, flow branches to 510 when the comparison indicates that the MSLV morphology and/or conduction pattern for the candidate beat matches and expected morphology or conduction pattern template. Alternatively, flow branches to 512 when the comparison indicates no match. At 510, the one or more processors of the IMD 100 label the candidate beat as an effective "capture" beat. For example, the IMD 100 may label the candidate beat as a capture beat when the at least one of the MSLV conduction pattern or MSLV morphology match the associated set of templates. At 512, the one or more processors of the IMD 100 label the candidate beat as a pseudo-fusion beat. When a candidate beat is labeled as a pseudo-fusion beat, the one or more processors also adjust the CRT programming configuration at 512. For example, the adjustment to the CRT pacing configuration may be to adjust the AV delay, the VV delay, RVLV delay, LVLV delay, a pacing amplitude, and/or other CRT parameters.

Following 510 and 512, flow may return to 504 where the IMD 100 continues to operate based on the original or adjusted CRT pacing configuration.

In accordance with embodiments herein, once templates are established for the 4 stimulus types, every subsequent beat (or ensemble average of a collection of beats) can be compared to the predefined conduction pattern templates and/or EGM morphology templates. Pseudo-fusion can then be verified if a paced beat fails to match an expected template. For example, if a BiV paced beat matches either the intrinsic or RV-only paced template more than it matches the BiV template, pseudo-fusion can be verified. Similarly, pseudo-fusion has occurred if an LV-only paced beat matches either the intrinsic or RV-only paced template more than it matches the LV-only template. Subsequently, whenever pseudo-fusion has been identified, the AVD and/or VVD can be progressively shortened until pseudo-fusion is no longer observed.

External Device

Figure 6:
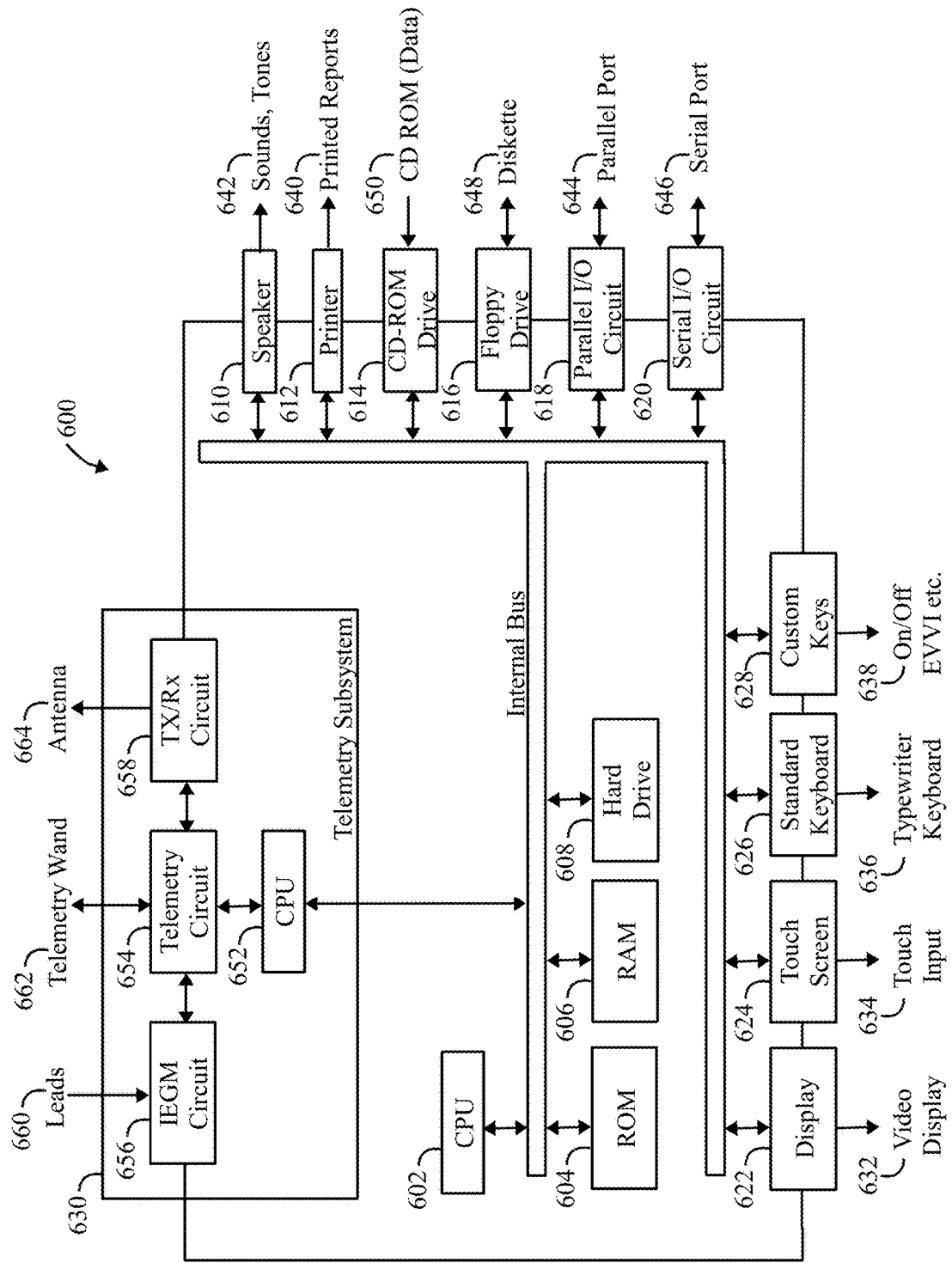
FIG. 6 illustrates a functional block diagram of the external device that is operated in accordance with the processes described herein and to interface with implantable medical devices as described herein.

FIG. 6 illustrates a functional block diagram of the external device 600 that is operated in accordance with the processes described herein and to interface with implantable medical devices as described herein. The external device 600 may be a workstation, a portable computer, an IMD programmer, a PDA, a cell phone and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates and detection thresholds. The RAM 606 may store, among other things, morphology templates, conduction pattern templates, cardiac signals, MSLV morphologies and conduction patterns in connection with candidate beats and the like.

The CPU 602 typically includes a microprocessor, a micro-controller, or equivalent control circuitry, designed specifically to control interfacing with the external device 600 and with the IMD 100. The CPU 602 may implement the processes described herein. For example, implanted leads (such as illustrated in FIG. 1) may be connected to an IEGM circuit 656 two collect cardiac signals in connection with candidate beats. Additionally or alternatively, cardiac signals may be received wirelessly through an antenna 164 that is communicating with an IMD. The CPU 602 may analyze the cardiac signals to identify MSLV morphology and conduction patterns in connection with candidate beats. The CPU 602 may compare the MSLV morphology and conduction patterns with morphology and conduction pattern templates in connection with labeling candidate beats as effective/capture beats and/or pseudo-fusion beats. The CPU 602 may adjust CRT parameters when pseudo-fusion beats are identified, as explained herein. The CPU 602 may include RAM or ROM memory, logic and timing circuitry, state machine circuitry, and I/O circuitry to interface with the IMD 100. The display 622 (e.g., may be connected to the video display 632). The touch screen 624 may display graphic information relating to the IMD 100. The display 622 displays various information related to the processes described herein. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 includes a central processing unit (CPU) 652 in electrical communication with a telemetry circuit 654, which communicates with both an IEGM circuit 656 and a transceiver (TX/RX) circuit 658. The circuit 656 may be connected to leads 660. The circuit 656 is also connected to the implantable leads 114, 116 and 118 to receive and process IEGM cardiac signals as discussed above. Optionally, the IEGM cardiac signals sensed by the leads 114, 116 and 118 may be collected by the IMD 100 and then transmitted, to the external device 600, wirelessly to the telemetry subsystem 630 input.

The telemetry circuit 654 is connected to a telemetry wand 662. The Tx/Rx circuit 658 includes communication circuits to communicate with antenna output 664. The external device 600 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 600 to the IMD 100.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method, comprising:
   under control of one or more processors,
   obtaining cardiac signals, associated with a candidate beat, from multiple electrodes distributed within the heart;
   processing the cardiac signals to collect at least one of a conduction pattern or a morphology;
   analyzing the at least one of the conduction pattern or morphology;
   labeling the candidate beat as a pseudo-fusion beat based on the analyzing the at least one of the conduction pattern or morphology.

2. The method of claim 1, wherein the analyzing includes comparing the at least one of the conduction pattern or morphology to one or more associated templates.

3. The method of claim 2, wherein the at least one of the conduction pattern or morphology represent at least one of a multi-site left ventricular (MSLV) conduction pattern or a MSLV morphology.

4. The method of claim 1, further comprising delivering, from an implantable medical device (IMD), cardiac resynchronization therapy (CRT) at one or more pacing sites and adjusting the CRT based on the labeling.

5. The method of claim 1, wherein the obtaining comprises obtaining the cardiac signals from multi-site left ventricular (MSLV) electrodes distributed along a left ventricle.

6. The method of claim 1, wherein the delivering includes delivering LV pacing, the one or more pacing sites includes one or more LV pacing sites.

7. The method of claim 1, wherein the labeling further comprises labeling the candidate beat as a capture beat when the at least one of the conduction pattern or morphology match an associated template.

8. The method of claim 7, wherein the templates comprise a set of morphology templates that include characteristics of interest from cardiac signals for multiple beats, the characteristics of interest including at least one of amplitudes of positive deflection local maximums, negative deflection local minimums, or zero crossings, the characteristics of interest further including characteristic timings with respect to a reference time-point.

9. The method of claim 1, wherein the conduction pattern comprises mean activation times associated with sensing vectors corresponding to the electrodes, and wherein the mean activation times are relative to a reference activation time.

10. The method of claim 7, wherein the LV activation times are associated with an RV-to-LVD1 activation interval, an RV-to-LVM2 activation interval, an RV-to-LVM3 activation interval, and an RV-to-LVP4 activation interval.

11. A system, comprising:
    an electrode combination;

memory to store program instructions;
one or more processors configured to implement the program instructions to:
obtain cardiac signals, associated with a candidate beat, from the electrode combination;
collect at least one of a conduction pattern or a morphology from the cardiac signals;
analyze the at least one of the conduction pattern or morphology; and
label the candidate beat as a pseudo-fusion beat based on the analyzing.

12. The system of claim 11, wherein the one or more processors are further configured to deliver cardiac resynchronization therapy (CRT) at one or more pacing sites from the electrode combination and adjust the CRT based on the labeling.

13. The system of claim 11, wherein the one or more processors are further configured to compare the at least one of the conduction pattern or morphology to one or more associated templates.

14. The system of claim 11, the at least one of the conduction pattern or morphology represent at least one of a multi-site left ventricular (MSLV) conduction pattern or a MSLV morphology.

15. The system of claim 11, wherein the one or more processors are further configured to obtain the cardiac signals from multi-site left ventricular (MSLV) electrodes distributed along a left ventricle.

16. The system of claim 11, wherein the one or more processors are further configured to label the candidate beat as a capture beat when the at least one of the conduction pattern or morphology match an associated template.

17. The system of claim 11, wherein the one or more processors are further configured to generate a set of the templates by:
a. cycling through CRT parameters for 1) Intrinsic conduction; 2) right ventricular-only pacing; 3) LV-only pacing and 4) Bi-ventricular (BiV) pacing;
b. sensing baseline cardiac signals from the MSLV electrodes in connection with each of the CRT parameters; and
c. analyzing the baseline cardiac signals to generate the set of templates, the set of templates to be utilized in the analysis of the at least one of the conduction pattern or morphology.

18. The system of claim 17, wherein each template from the set of templates is generated based on averages for characteristics of interest from the cardiac signals for multiple beats associated with corresponding stimulus.

19. The system of claim 13, wherein the templates comprise a set of morphology templates that include characteristics of interest from cardiac signals for multiple beats, the characteristics of interest including at least one of amplitudes of positive deflection local maximums, negative deflection local minimums, or zero crossings, the characteristics of interest further including characteristic timings with respect to a reference time-point.

20. The system of claim 11, wherein the conduction pattern comprises mean activation times associated with sensing vectors corresponding to the MSLV electrodes, and wherein the mean activation times are relative to a reference activation time.

21. The system of claim 20, wherein the activation times are associated with at least two of an RV-to-LVD1 activation interval, an RV-to-LVM2 activation interval, an RV-to-LVM3 activation interval, or an RV-to-LVP4 activation interval.

22. The system of claim 11, wherein the morphology comprises unipolar or far-field morphologies for cardiac signals collected along sensing vectors that comprise at least one of RV-Can/Coil, LVD1-Can/Coil, LVM2-Can/Coil, LVM3-Can/Coil, or LVP4-Can/Coil.

23. The system of claim 11, wherein the one or more processors is configured to adjust at least one parameter that defines a cardiac resynchronization therapy when the candidate beat is labeled the pseudo-fusion beat.

24. The system of claim 11, further comprising at least one of an implantable medical device, external device or server, the one or more processors at least partially housed within the at least one of an implantable medical device, external device or server.

* * * * *